United States Patent
Yunoki et al.

(10) Patent No.: US 8,303,519 B2
(45) Date of Patent: Nov. 6, 2012

(54) GUIDE WIRE HAVING MARKINGS TO INDICATE CHANGES IN STRUCTURAL FEATURES

(75) Inventors: Seiko Yunoki, Fussa (JP); Kenji Shibaki, Hachioji (JP); Masayuki Iwasaka, Tama (JP)

(73) Assignee: Olympus Corporation, Tokyo (JP)

( * ) Notice: Subject to any disclaimer, the term of this patent is extended or adjusted under 35 U.S.C. 154(b) by 729 days.

(21) Appl. No.: 11/230,038

(22) Filed: Sep. 19, 2005

(65) Prior Publication Data

US 2006/0015040 A1   Jan. 19, 2006

Related U.S. Application Data

(63) Continuation of application No. PCT/JP03/03642, filed on Mar. 25, 2003.

(51) Int. Cl.
*A61M 25/00* (2006.01)
*A61M 5/178* (2006.01)
*A61B 1/00* (2006.01)
*A61B 1/04* (2006.01)

(52) U.S. Cl. ... 600/585; 600/114; 600/101; 604/164.01; 604/164.13

(58) Field of Classification Search ......... 600/585, 600/101, 103, 104, 105, 114, 117; 604/103.1, 604/117, 164.13, 523
See application file for complete search history.

(56) References Cited

U.S. PATENT DOCUMENTS

| | | | |
|---|---|---|---|
| 4,676,249 A | 6/1987 | Arenas et al. | |
| 4,682,607 A * | 7/1987 | Vaillancourt et al. | 600/585 |
| 5,084,022 A | 1/1992 | Claude | |
| 5,253,653 A | 10/1993 | Daigle et al. | |
| 5,320,602 A * | 6/1994 | Karpiel | 604/514 |
| 5,379,779 A | 1/1995 | Rowland et al. | |
| 5,479,938 A | 1/1996 | Weier | |
| 5,498,250 A * | 3/1996 | Prather | 604/529 |
| 5,599,300 A | 2/1997 | Weaver et al. | |
| 5,836,893 A * | 11/1998 | Urick | 600/585 |
| 5,916,178 A | 6/1999 | Noone et al. | |
| 6,036,682 A * | 3/2000 | Lange et al. | 604/529 |
| 6,613,002 B1 * | 9/2003 | Clark et al. | 600/593 |
| 7,278,973 B2 * | 10/2007 | Iwami et al. | 600/585 |

FOREIGN PATENT DOCUMENTS

| | | |
|---|---|---|
| JP | 4-108556 | 4/1992 |
| JP | 9-94298 | 4/1997 |
| JP | 11-89940 | 4/1999 |
| JP | 11-137693 | 5/1999 |
| JP | 2001-46508 | 2/2001 |

* cited by examiner

*Primary Examiner* — Max Hindenburg
*Assistant Examiner* — Adam Eiseman
(74) *Attorney, Agent, or Firm* — Scully, Scott, Murphy & Presser, PC

(57) ABSTRACT

This invention provides a guide wire whose structural features can be determined through an endoscope. The guide wire is inserted into a patient's body and used in the lumen. It has markings at the positions where the structural features change.

11 Claims, 3 Drawing Sheets

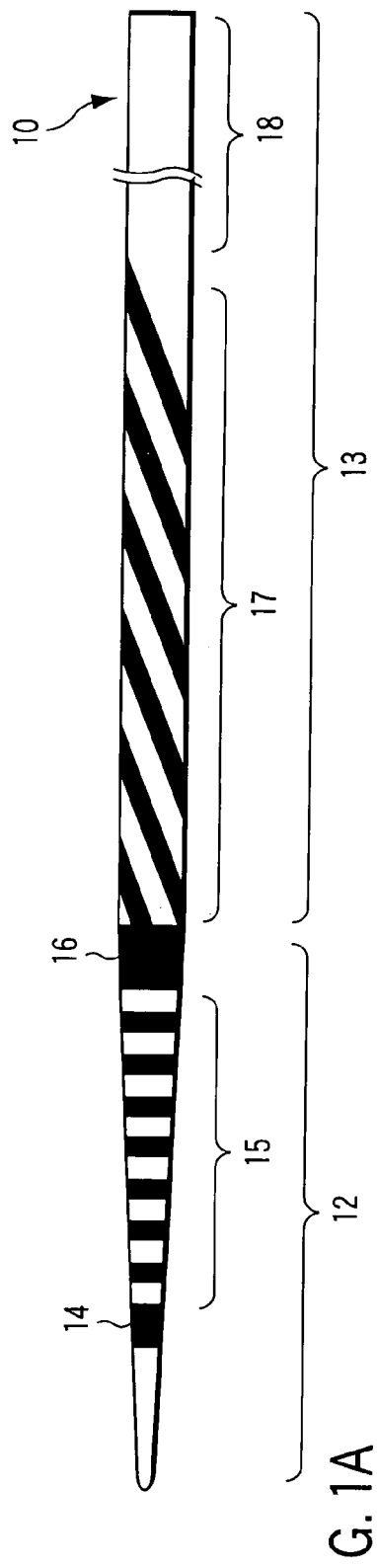
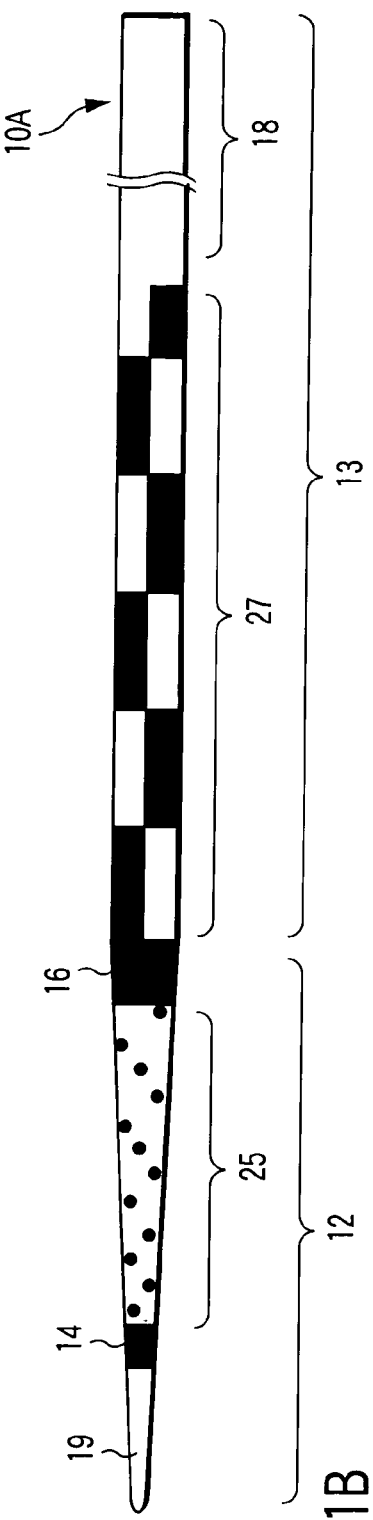
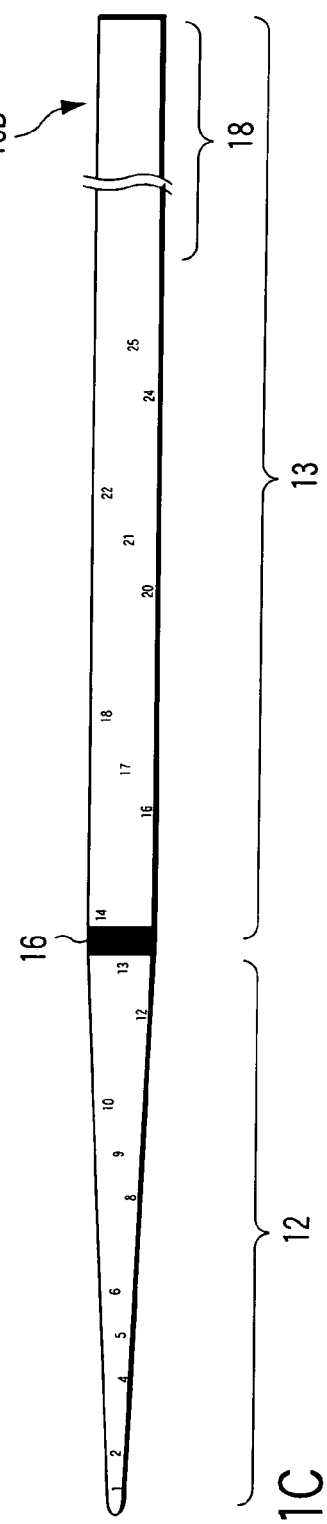

GUIDE WIRE HAVING MARKINGS TO INDICATE CHANGES IN STRUCTURAL FEATURES

CROSS-REFERENCE TO RELATED APPLICATIONS

This is a Continuation Application of PCT Application No. PCT/JP03/03642, filed Mar. 25, 2003, which was published under PCT Article 21(2) in Japanese.

BACKGROUND OF THE INVENTION

1. Field of the Invention

The present invention relates to a guide wire for use in medical treatments. More particularly, it relates to a guide wire that is used to make an approach through the duodenal papilla to the pancreatic obiliary duct, by using an endoscope inserted through the mouth.

2. Description of the Related Art

Various types of guide wires are generally known. Some have desired flexibility, each formed by coiling a wire of metal such as stainless steel. Others have a tapered distal part, each made of a single wire of super elastic metal such as nickel-titanium alloy.

Such a guide wire is used to guide an instrument, such as catheter, into a narrow tract or lumen, or to replace the catheter with another. The guide wire may have marking that is fit to the specific use of the guide wire.

U.S. Pat. No. 5,084,022, for example, discloses a guide wire that has marks provided at regular intervals. The mark intervals serve to measure the length of an object.

Jpn. UM Appln. KOKAI Publication No. 4-108556 and Jpn. Pat. Appln. KOKAI Publication No. 2001-46508 disclose guide wires having marking that may be used to confirm the depth to which an instrument is inserted into, for example, the papilla.

U.S. Pat. No. 5,379,779 discloses a guide wire having marking that may be used to determine whether the guide wire moves or not while the catheter is being replaced by another.

Jpn. Pat. Appln. KOKAI Publication No. 11-89940 and Jpn. Pat. Appln. KOKAI Publication No. 11-137693 discloses guide wires having an angled part at the distal end. These guide wires have marking that enables the user to determine visually the position or orientation of the angled part.

The marking on any conventional guide wire described above helps the user to determine mainly the posture, position or motion of the guide wire.

However, the conventional guide wires having marking are disadvantages in the following respects.

A first disadvantage will be explained with reference to FIG. 3A.

To replace a catheter inserted in the papilla with another catheter, only the catheter (not shown) is usually pulled back, pulling its distal end into the endoscope 102, while the guide wire remains inserted in the papilla. Then, the hebel 103 at the distal end of the endoscope is raised to the uppermost position, bending the guide wire 1 and fastening the same to the endoscope.

When the guide wire 1 is bent at the distal part, the force fastening the wire 1 to the endoscope cannot be sufficient because the distal part is soft. If the guide wire 1 is bent at the distal part that is soft, the fastening force is so small that the guide wire 1 may move in the direction of the arrow while the catheter is being replaced with another. If the guide wire 1 is so moves, it may slip from the papilla or a narrow tract.

A second disadvantage will be explained, with reference to FIG. 3B.

Assume that a stent (not shown) or a catheter 104 mounted on a guide wire 1 is being inserted into the capilla or the like. If the distal part of the guide wire 1 has been inserted a little into the capilla, the stent or catheter is more rigid than the distal part of the guide wire 1. Hence, the guide wire is straightened along the stent or catheter and is no longer bent.

As the stent or catheter 104 is moved forward in this condition, the distal part of the guide wire 1 may slip from the papilla. Then, the catheter can no longer be replaced in some cases. The distal part of the guide wire may be coated with lubricant for smooth insertion. In this case, the guide wire will be more likely to slip from the papilla if an error is made, however small the error is, in manipulating the stent or catheter while only the distal end of the guide wire remains inserted in the papilla.

The position that the distal end of the conventional guide wire takes with respect to the endoscope cannot be confirmed while the guide wire is being manipulated, even though the guide wire has marking. It is therefore demanded that the guide wire be improved in operability.

BRIEF SUMMARY OF THE INVENTION

The present invention has been made in view of the foregoing. An object of the invention is to provide a guide wire that excels in operability because it has marking that helps to observe its structural features through an endoscope.

A guide wire according to this invention is designed to achieve the object. The guide wire is to be inserted into a lumen of the patient and used therein. It is characterized by the marking provided on that part which undergoes structural changes.

The present invention provides a guide wire to be inserted into a lumen of the patient and used therein, which is characterized by marking showing a specific position and provided on that part which lies at a distance of 60 mm to 400 mm from the distal end.

That part of the guide wire according to this invention, which undergoes structural changes, extends from the highly flexible distal part to the greatly rigid proximal portion.

BRIEF DESCRIPTION OF THE SEVERAL VIEWS OF THE DRAWING

FIGS. 1A to 1C are diagrams explaining various types of guide wires according to preferred embodiments of this invention;

DETAILED DESCRIPTION OF THE INVENTION

Figure 2A:
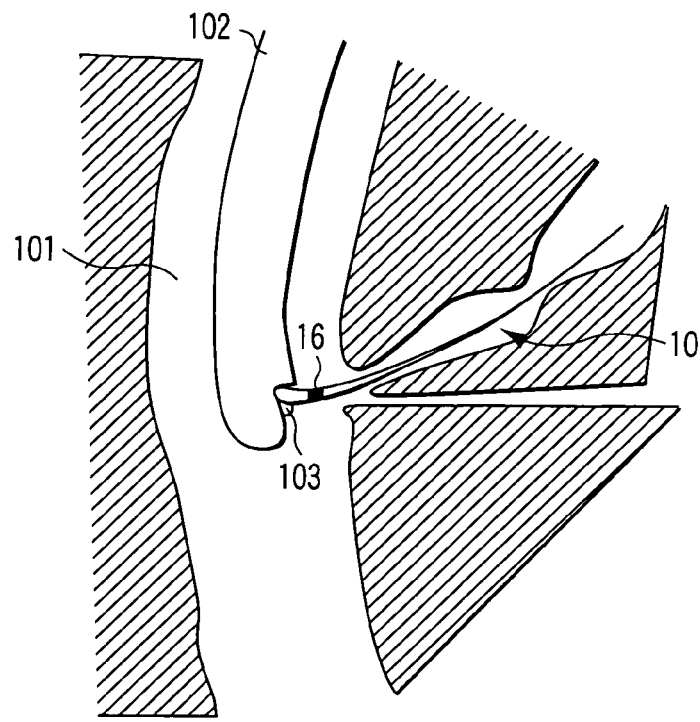
FIGS. 2A and 2B are diagrams showing how a guide wire according to an embodiment of the invention is used.

A first embodiment of this invention will be described.
(Structure)

First, the structure of the first embodiment will be described, with reference to FIG. 1A.

A guide wire 10 according to this embodiment comprises a core wire made of a single wire of nickel-titanium alloy, which is coated with urethane resin.

The guide wire 10 has a distal part 12 and a proximal part 13. The distal part 12 is flexible. The proximal part 13 is greatly rigid. The distal part 12 attains flexibility, because it is tapered by means of, for example, center-less polishing. The center-less polishing is performed over an appropriate distance, about 150 mm from the distal end in the present embodiment.

The guide wire 10 has markings 14, 15, 16 and 17. The marking 14 is a broad ring provided at a distance of, for example, 70 mm from the distal end. The marking 15 consists of ring-shaped markers arranged at regular intervals of 3 mm, each having a width of, for example, 2 mm. The marking 16 is a broad ring provided at a distance of, for example, 150 mm from the distal end. The marking 17 is a spiral marker having a width of, for example, 2 mm. The proximal part 18, starting 15 at 250 mm from the distal end, has no marking.

The broad-ring marking 14 indicates a particular depth to which or beyond which the distal part 12 should be inserted into, for example, the papilla, lest it should slip from the papilla. In view of this, the position of the marking 14 is not limited to the one shown in FIG. 1A. The marking 14 can be provided at any other position, if it indicates the particular depth. The position the marking 14 should take can be determined by the characteristic in structure or rigidity of the guide wire 10, such as the tapering angle. It is desired that the marking 14 be a ring-like shape that uninterruptedly extends around the guide wire 10, and have such a shape and such a size as can be reliably seen, in whichever manner it is bent.

The mark 15, which consists of ring-shaped markers arranged at intervals, makes it easy to determine whether the guide wire 10 is moving in the axial direction. The marking 17, which is a spiral marker, makes it easy to determine whether the guide wire 10 is rotating. The markings 15 and 17 may be of any shapes other than those shown, provided they enable the user to determine in which direction the guide wire 10 is moving or rotating. The markings 15 and 17 may have the same shape or pattern. If they have different patterns as in this embodiment, they can help identify the distal part 12 and the proximal part 13, respectively. Consisting of ring-shaped markers arranged at intervals, the marking 15 helps the user to determine accurately how much the guide wire 10 has moved in its axial direction.

The marking 16, i.e., the broad ring provided between the markings 15 and 17, indicates the position at which the flexible distal part 12 terminates and the rigid proximal part 13 starts. Thus, the marking 16 will be located at a different position if the distal part 12, which is tapered, is lengthened or shortened.

(Function and Advantage)

The function and advantage of the markings provided on the guide wire 10 described above will be explained, with reference to FIG. 1A and FIGS. 2A and 2B.

The guide wire 10 may be inserted, as the conventional guide wire, from the papilla into the pancreatic obiliary duct, through an endoscope 102 inserted in, for example, the duodenum. In this case, the surgeon or operator inserts the guide wire 10 into the papilla, while observing the most distal marking 14 through the endoscope 102. Since the marking 14 is shaped like a broad ring, it can easily be recognized whichever position the distal part 12 takes, or no matter whether the distal part 12 is inclined or rotated.

Once the marking 14 has been inserted into the papilla, it can no longer be seen through the endoscope 102. This indicates that the guide wire 10 has been inserted into the papilla to a sufficient depth. If the operator manipulates the guide wire 10, the distal part 12 will not slip out of the papilla. If the marking 14 is seen in the view field of the endoscope 102, it indicates that the distal part 12 has not been sufficiently inserted into the papilla or has been pulled too much from the papilla. Thus, the operator can know that the distal part 12 may slip from the papilla if he or she manipulates the guide wire 10 in this condition.

As indicated above, the marking 15 consists of ring-shaped markers arranged at intervals and the marking 17 is a spiral marker. Hence, the marking 15 enables the operator to determine how the guide wire 10 is moving in its axial direction, and the marking 17 enables the operator to determine how the guide wire 10 is rotating. If the operator knows the width of the ring-shaped markers, he or she can easily determine how long the wire 10 has moved.

Figure 2B:
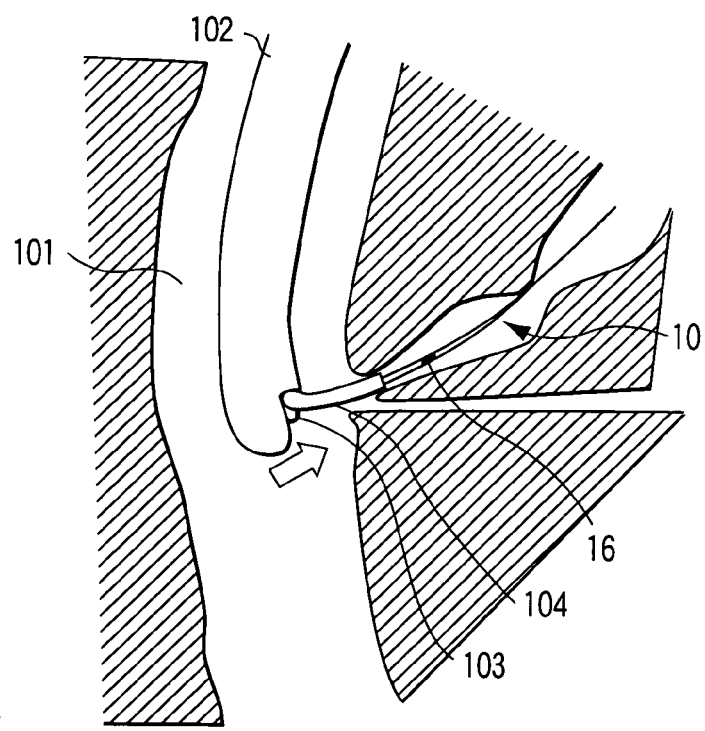
Figure 3A:
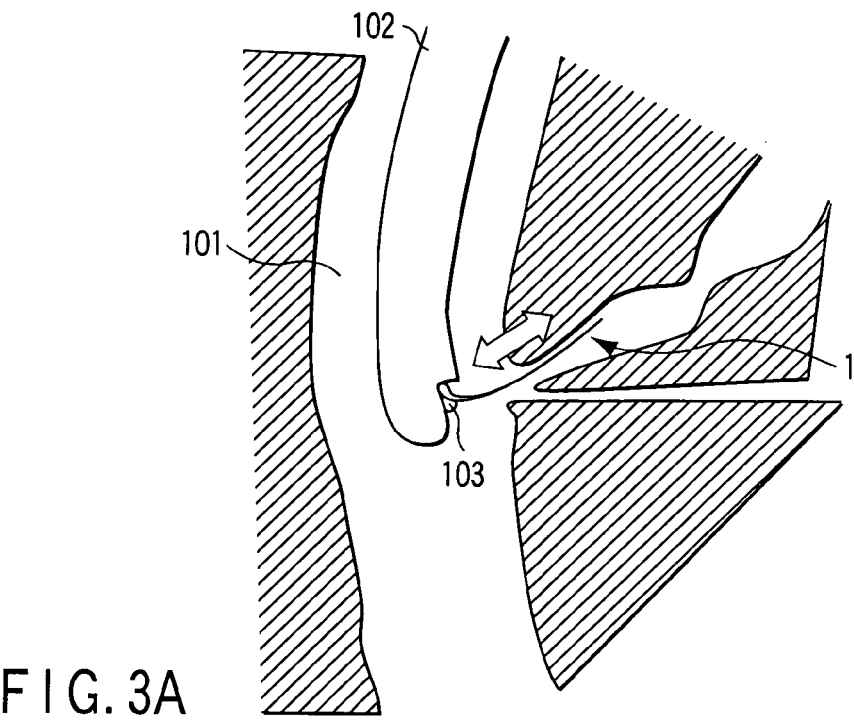
FIGS. 3A and 3B are diagrams showing how a conventional guide wire is used.
Figure 3B:
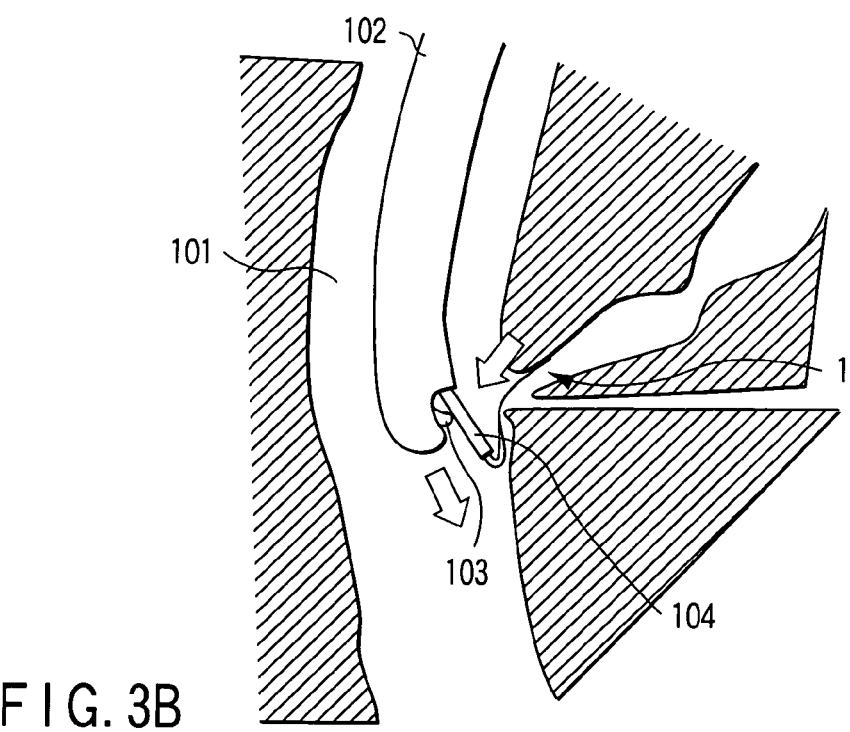

FIG. 2A illustrates how a catheter 104 is replaced by another, by using the guide wire 10. First, an endoscope 102 inserted into, for example, the duodenum 101 as shown in FIG. 2A. Then, the catheter 104 is pulled into the endoscope 102, leaving the guide wire 10 in the duodenum 101 in the same way as the conventional guide wire. The catheter 104 can no longer be seen in the view field of the endoscope 102. Only the guide wire 10 is seen in the view field.

Observing the marking 16 on the guide wire 10 through the endoscope 102, the operator raises the hebel 103 to the uppermost position. While the marking 16 remains in the view field of the endoscope 102, not only the flexible distal part 12, but also the rigid proximal part 13 projects from the endoscope 102 to a position near the hebel 103. Hence, the rigid proximal part 13 is bent when the hebel 103 is raised. Therefore, the proximal part 13 is reliably secured to the endoscope 102.

Since the guide wire 10 has its proximal part 13 bent and is therefore is firmly secured to the endoscope 102, only the catheter 104 can be pulled from the endoscope 102. After pulling the catheter 104, another catheter (not shown) can be inserted into the endoscope 102.

If the marking 16 is inserted in the papilla when the catheter 104 is inserted into the papilla, that part of the guide wire 10 which is exposed, extending from the forceps port of the endoscope 102 to the entrance of the papilla, has sufficient rigidity.

As the catheter 104 is further moved forward in this condition, it advances along the guide wire 10 and can be easily inserted into the capilla. This is because that part of the guide wire 10 which lies near the capilla is far more rigid than the catheter 104.

The rigidity of any part of the guide wire 10 can therefore be determined through the endoscope. Further, it can be determined whether the part of the wire 10 is moving forward or backward and whether it is rotating or not. This helps the operator to manipulate the guide wire 10 easily and reliably. The guide wire 10 is greatly improved in operability.

A second embodiment of this invention will be described. The components identical or similar to those of the first embodiment are designated at the same reference numerals and will not be described in detail.

(Structure)

As FIG. 1B shows, a guide wire 10A according to this embodiment comprises a single wire made of nickel-titanium alloy, having a tapered distal end and coated with urethane resin. A part of the distal end has a lubricant coating 19.

The present embodiment has marking 14 and marking 16. The marking 14 is provided on the proximal end of the lubricant coating 19. The marking 16 is provided on the junction between the flexible distal part 12 and the rigid proximal part 13. Marking 25, consisting of polka dots is provided on that part of the distal part 12, which extends between the marking 14 and the making 16. Marking 27, or a checkered pattern, is provided on the proximal part 13, adjacent to the marking 16.

The marking 14 serves to prevent the guide wire 10A from slipping out of the papilla as in the first embodiment, due to an error made in manipulating the guide wire 10A. Unlike the marking 14 on provided on the first embodiment, which helps to determine the depth to which the wire has been inserted, the marking 14 helps to determine whether the lubricant coating 19 on the distal end of the guide wire 10A is completely inserted in the papilla.

Using the marking 14, the operator can determine whether the lubricant coating 19 has been completely inserted into the papilla or not. Hence, he or she can prevent the guide wire 10A from slipping out of the papilla against his or her intension, while he or she is manipulating the guide wire 10A.

The marking 25, located between the marking 14 and the marking 16, consists of many small makers, i.e., polka dots. Therefore, the marking 25 enables the operator to determine not only how the guide wire 10A is moving forward or backward, but also how it is rotating. Since the polka dots are arranged at specific intervals in the axial direction of the wire, the marking 25 can be used to determine how long the guide wire 10A has moved, as in the first embodiment.

Generally, any marking on a guide wire of this type should have bright color so that it may be well seen through the endoscope. If the marking is of bright color, however, it excessively reflects the intense light coming from the light source provided in the endoscope. Inevitably, the object of interest appears white in the view field of the endoscope and can hardly be recognized. (Hereinafter, this phenomenon will be referred to as "halation.") Hence, it is desired that the guide wire 10A has dark color and a small amount of markings of bright color are applied to the guide wire.

In the present embodiment, the markers, i.e., polka dots, are small and of bright color. This much serves to prevent halation.

The marking 27 provided on the proximal part 13 is a checkered pattern. Like the marking 25, this marking 27 can be used to determine how the guide wire 10A is moving forward or backward, how it is rotating, and how long the guide wire 10A has moved.

(Function and Advantage)

The guide wire 10A according to this embodiment can be used in the same manner as the first embodiment. In this embodiment, the guide wire 10A has lubricant coating 19. Thus, the marking 14, which is provided at the boundary between the distal part having the lubricant coating 19 and the proximal part having no lubricant coating, where the surface condition changes, may be used in place of, or together with, the markings 14 and 16 of the first embodiment, whose shapes indicate a position where the structural feature changes. Then, the marking 14 can serve to determine the lubricity.

Thus, the lubricity and rigidity of the guide wire 10A can be determined from the marking 14, marking 16, marking 25 and marking 27 all observed through the endoscope. This improves the operability of the guide wire 10A.

A third embodiment of this invention will be described.

(Structure)

This embodiment will be described, with reference to FIG. 1C.

A guide wire 10B according to this embodiment has marking 16 identical to the marking 16 provided on the first embodiment. The wire 10B has no marking similar to the other markings provided on the first embodiment. Instead, it has small numerals used as markers, which are arranged in a helical line.

It is desired that the numerals should represent distances from the distal end. Nonetheless, they may represent other values. They may be spaced at regular intervals or any other type of intervals.

The markers are not limited to numerals. They may be markers of any other type, e.g., characters or symbols, which can be recognized through the endoscope.

(Function and Advantage)

Having numerals arranged in a helical line, the guide wire 10B according to this embodiment achieves the same advantage as the two embodiments described above.

The marking 14 and marking 16 on the guide wire 10A according to the second embodiment have been provided by the manufacturer. The operator must manipulate the guide wire 10A in accordance with the marking 14 and the marking 16. On the other hand, the small numerals on the guide wire 10B according to this embodiment may assume whatever significance the operator selects in accordance with his or her taste or the patient's condition. In accordance with the numerals, the operator can manipulate the wire 10B.

If the operator wants to secure a soft part of the guide wire 10B at the hebel 103, he or she secures a flexible part of the guide wire 10B, which is more distal than the marking 16. In this case, the operator may manipulate the guide wire, using any small numeral, for example "9" as reference mark, instead of the marking 16.

It is desired that the markings 14, 15, 16 and 17 on the guide wire 10 (first embodiment) and the markings 25 and 27 on the guide wired 10A (second embodiment), which indicate specific positions, and the marking on the guide wire 10B (third embodiment), which consists of numerals, characters or symbols, should be provided at positions in a range between 60 mm and 400 mm from the distal end of the guide wire. This is because the guide wire would not be inserted to a depth beyond 400 mm from the papilla and because no advantages result if its structural features, such as flexibility, are sharply changed at a distance within 60 mm from the distal end. If its structural features are so changed, its behavior is unstable and may not be easily inserted. Thus, the marking should better be provided in said range.

In the case where such marking as described above is provided at a position where the guide wire changes in structural features, the position where the structural features change is not limited to one that is based on shape. The position can be one at which the surface condition changes. For example, it is the boundary between the distal part having lubricant coating and the proximal part that having no lubricant coating.

As can be seen from the foregoing, the structural feature of each guide wire according to this invention can be determined through an endoscope. This can prevent the guide wire from slipping from the capilla while the guide wire is being manipulated and can ultimately improve the operability of the guide wire.

This invention has been described, in conjunction with various preferred embodiments shown in the figures. Other embodiments similar to those described above can be implemented. Further, the embodiments described above can be modified to perform the same function as this invention. Namely, this invention is not limited to any one of the embodiments described above. The embodiments can be combined in various ways, within the intended scope of this invention.

What is claimed is:

1. A guide wire which has an outer surface including a tapered distal end part and which is to be inserted into a patient's body through an endoscope including a hebel in a distal end part and used in a lumen, the guide wire comprising:

an elongated core wire, which is made of a single wire and which has a distal end extending to a distal end of the guide wire, and a proximal end;

a distal end part, which extends between a predetermined part and the distal end of the core wire and which is tapered toward the distal end;

a proximal end part, which extends between the predetermined part and the proximal end of the core wire;

a first marking located on the outer surface and visible through the endoscope, the first marking representing a position suitable for bending at the hebel, wherein the guide wire is more rigid in a proximal end side of the first marking than a distal end side, and configured to be reliably secured to the endoscope, when the guide wire is bend with the hebel in a state where the first marking is seen in a view filed of the endoscope; and a second marking located on the outer surface and visible through the endoscope, the second marking representing a guide to prevent the distal end part inserted in the lumen from slipping out of the lumen, wherein the second marking allows observation of a position where at least one of the flexibility and surface condition of the guide wire changes through the endoscope.

2. The guide wire according to claim 1, further comprising a third marking, which allows observation of a rotation of the guide wire through the endoscope when the guide wire rotates in the patient's body.

3. The guide wire according to claim 2, wherein the third marking is a spiral marker provided at a proximal end side of the first marking.

4. The guide wire according to claim 2, wherein the third marking is a checked pattern provided at a proximal end side of the first marking.

5. The guide wire according to claim 2, wherein the third marking is a series of small numerals.

6. The guide wire according to claim 5, wherein the small numerals represent distances from the distal end of the guide wire.

7. The guide wire according to claim 2, further comprising a fourth marking, which is formed between the first marking and the second marking and which allows observation of movement of the guide wire in an axial direction through the endoscope.

8. The guide wire according to claim 7, wherein the fourth marking is formed of a plurality of rings arranged at regular intervals along the axial direction.

9. The guide wire according to claim 7, wherein the fourth marking is formed of polka dots.

10. The guide wire according to claim 9, wherein the polka dots have a color brighter than that of the outer surface of the guide wire.

11. The guide wire according to claim 1, wherein the core wire is coated with urethane resin.

* * * * *